United States Patent [19]
Howard

[11] Patent Number: 5,824,291
[45] Date of Patent: Oct. 20, 1998

[54] CHEWING GUM CONTAINING A TEETH WHITENING AGENT

[75] Inventor: Herman S. Howard, Stamford, Conn.

[73] Assignee: Media Group, Stamford, Conn.

[21] Appl. No.: 885,226

[22] Filed: Jun. 30, 1997

[51] Int. Cl.⁶ .............................. A61K 9/68; A61K 7/16; A61K 7/20; A61K 7/26

[52] U.S. Cl. .............................. 424/48; 424/53; 424/58; 424/440; 426/3

[58] Field of Search .................. 424/440, 48, 49–58, 424/195.1

[56] References Cited

U.S. PATENT DOCUMENTS

| | | | |
|---|---|---|---|
| H1541 | 6/1996 | Holla | 424/195.1 |
| 3,860,734 | 1/1975 | Huth et al. | 426/369 |
| 3,886,265 | 5/1975 | Evers et al. | 424/49 |
| 4,012,531 | 3/1977 | Viani | 426/431 |
| 4,132,770 | 1/1979 | Barth | 424/49 |
| 4,423,030 | 12/1983 | Hayes et al. | 424/58 |
| 4,496,592 | 1/1985 | Kuwahara et al. | 426/5 |
| 4,572,836 | 2/1986 | Bakal | 426/321 |
| 4,759,936 | 7/1988 | Best et al. | 426/250 |
| 4,812,308 | 3/1989 | Winston et al. | 424/52 |
| 5,248,503 | 9/1993 | Emanuel-King | 424/195.1 |
| 5,371,254 | 12/1994 | Lidert | 424/195.1 |
| 5,424,060 | 6/1995 | Hauschild | 424/52 |
| 5,464,608 | 11/1995 | Khartchenko et al. | 424/53 |
| 5,472,684 | 12/1995 | Nabi et al. | 424/49 |
| 5,525,340 | 6/1996 | Fukunaga | 424/195.1 |
| 5,648,064 | 7/1997 | Gaffar et al. | 424/53 |
| 5,693,334 | 12/1997 | Miskewitz | 424/440 |

FOREIGN PATENT DOCUMENTS 60-207664  10/1985  Japan .

OTHER PUBLICATIONS

Lewis et al "Medical Botany—Plants Affecting Mans Heart" John Wiley & Sons RS 164 L 475 pp. 246 247 269 270 Neem Toothpaste Nimodent Toothpegdir 1977.

Iwu "Handbook of African Medicinal Plants" CRC Press Boca Raton, Fla pp. 124 to 128, 364 Azadirachta Indica Medkua Azadirachta Neem Margusa Silvose 1993.

Reynolds Martindale, The Extra Pharmacopoeia 13th Ed. London The Pharmaceutical Press p. 1340 Azadirachta, Margusa, Neem 1993.

*Primary Examiner*—Shep K. Rose
*Attorney, Agent, or Firm*—Evelyn M. Sommer

[57] ABSTRACT

A chewing gum composition for whitening teeth comprising a water insoluble gum base in admixture with a plasticizer, a flavorant, sweetener, filler, texturizer, color, stabilizer, surface active agent and the like, some of the foregoing being optional, and a safe and effective whitening amount of a water soluble alkali metal percarbonate, a safe and effective amount of neem oil, sodium bicarbonate and parsley extract.

14 Claims, No Drawings

CHEWING GUM CONTAINING A TEETH WHITENING AGENT

This invention relates generally to a chewing gum composition which when chewed by an individual acts to whiten teeth and more particularly to a chewing gum composition for whitening teeth that is more effective than existing products available to the consumer.

A tooth is comprised of an inner dentin layer and an outer hard enamel layer that is the protective layer of the tooth. The enamel layer of a tooth is naturally an opaque white or slightly off-white color. It is this enamel layer that can become stained or discolored. The enamel layer of a tooth is composed of hydroxyapatite mineral crystals that create a somewhat porous surface. It is believed that this porous nature of the enamel layer is what allows staining agents and discoloring substances to permeate the enamel and discolor the tooth.

Many substances that an individual comes in contact with on a daily basis can "stain" or reduce the "whiteness" of his or her teeth. In particular, foods, tobacco products and fluids such as tea and coffee tend to stain the teeth. These products or substances accumulate on the enamel layer of the tooth and form a pellicle film over the teeth. These staining and discoloring substances can then permeate the enamel layer.

One method for whitening teeth used by dental professionals involves the use of 30% hydrogen peroxide in combination with heat and light to promote an oxidation reaction. This method, although fast, is losing favor with dentists because clinical and scientific evidence shows that an effective whitening process without heat and light is desired.

Another professional method for bleaching teeth involves the use of hydrogen peroxide generating compounds such as urea peroxide (carbamide peroxide) at concentrations of 10% to achieve the desired whitening effect. Urea peroxide rapidly breaks down into hydrogen peroxide due to the water present in saliva. This method is known as an office-monitored at-home bleaching system and involves the use of a mouth guard or tray within which the bleaching agent is placed. The tray is then placed over the teeth of the user and bleaching is allowed to take place. This method of treatment has drawbacks including tooth sensitivity possibly due to demineralization, and irritation of oral tissues. An additional disadvantage of the tray application method is that the bleaching takes place very slowly.

There is a demand in the marketplace for a tooth whitening product that can be used at home, at work, while traveling or exercising by the consumer and is safe and easy to use.

Chewing gum if it could be adapted to effectively achieve this goal would be such a product.

Chewing gum generally consists of a water insoluble gum base and a water soluble portion along with flavors i.e., flavoring agents. The water soluble portion and flavors dissipate during chewing and the gum base is retained in the mouth throughout the chew.

The gum base constituting the chewing gum composition is preferably an ordinary gum base similar to those which are commonly used. Depending on whether it is a chewing pastille, chewing gum stock or a low-calorie chewing gum, the gum base may represent approximately 15% to approximately 70% of the composition in accordance with the invention. Its nature will also be adapted to the type of chewing gum manufactured.

The water insoluble gum bases for use herein are disclosed for example in U.S. Pat. Nos. 3,052,552 and 2,197,719.

The insoluble gum base generally comprises elastomers, resins, fats and oils, softeners, stabilizers, thickeners, surface active agents, and inorganic fillers. Elastomers can include synthetic elastomers including polyisobutylene, isobutyleneisoprene copolymers, styrenebutadiene copolymers, polyvinyl acetate, polyisoprene, polyethylene, vinyl acetate - vinyl laurate copolymers, and combinations thereof. Natural elastomers that can be used include natural rubber.

The gum base can include elastomer plasticizers. Such elastomer plasticizers can include natural rosin esters, as well as other elastomer plasticizers. Additionally, the gum base can include fillers/texturizers and softeners/emulsifiers. Softeners are added to chewing gum in order to optimize the chewability and mouth feel of the gum. Softeners/emulsifiers that are typically used include tallow, hydrogenated tallow, hydrogenated and partially hydrogenated vegetable oils, cocoa butter, glycerol monostearate, glycerol triacetate, lecithin, and combinations thereof. Such material is required to be "ingestibly" acceptable and thus non-toxic or otherwise non-deleterious. Particularly critical is the additional requirement that such material be organoleptically compatible with the peroxide source, for example, encompassed within the scope of our invention. Also critical is the additional requirement that such material be nonreactive (within the range of storage conditions and room temperature use conditions) with the alkali metal percarbonate, the peroxide source of the invention.

Thus, in addition to a water insoluble gum base portion, a typical chewing gum composition includes a water soluble portion and one or more flavoring agents. The water soluble portion can include bulk sweeteners, high intensity sweeteners, flavoring agents, stabilizers, softeners, surface active agents, emulsifiers, colors, acidulants, fillers, antioxidants, and other components that provide desirable attributes.

All of the materials are well known in the art for such use being extensively described in the relevant literature. Sweeteners may be sugars, including sucrose or dextrose and/or artificial sweeteners including dipeptides, cyclamates and saccharin. The content of sweeteners, flavoring agents, stabilizers, etc. can amount to approximately 27 to approximately 82% of the composition.

It is known to use hydrogen peroxide or hydrogen peroxide generating compounds such as urea peroxide (carbamide peroxide), sodium perborate metal peroxides, for example, $SrO_2 CaO_2$ and $NaO_2$, in oral formulations such as mouth rinses and tooth pastes. These oral compositions are generally packaged as dilute aqueous solutions or as a dental composition which contains liquids and solids. The liquid content may be about 5–90% by weight.

One of the major disadvantages associated with the use of oral compositions for whitening teeth containing hydrogen peroxide or a hydrogen peroxide generating compound is their relative instability.

Dilute 1% aqueous solutions of hydrogen peroxide or hydrogen peroxide generating compound will substantially decompose in as little as 30 days at ambient temperatures. Storage at 3° C., significantly improves stability but not to the extent required for the normal market age for a consumer or professional product. In addition, many common adjuvants present in consumer and professional products such as flavorants and other organic materials can rapidly react with hydrogen peroxide or hydrogen peroxide generating compound, destroying both the adjuvants and the hydrogen peroxide or hydrogen peroxide generating compound.

The present invention provides a novel chewing gum composition for whitening teeth comprising a gum base in admixture with plasticizers or softening agents, flavorants, sweeteners and other optional ingredients, a safe and effective whitening amount of a water soluble alkali metal percarbonate such as sodium or potassium percarbonate, a safe and effective amount of neem oil, sodium bicarbonate and parsley extract. The preferred peroxide source is sodium percarbonate, also referred to as sodium carbonate peroxyhydrate, having the chemical formula 2 $Na_2$ $CO_3$ $3H_2O_2$. This material is particularly preferred because it is highly water soluble and dissolves quickly to generate hydrogen peroxide and also provides a source of alkalinity in the mouth. The percarbonate component is commercially available in fine powder form in both technical and pharmacological grades.

The amount of alkali metal percarbonate incorporated into the chewing gum compositions ranges from about 0.01 to about 0.75% by weight and preferably from about 0.10 to about 0.50% by weight of the total gum composition.

Neem oil is obtained as an extract from neem tree seeds. The neem seed extracts contain azadirachtin as the active ingredient. There are various methods known in the prior art to extract the neem oil from neem seeds. Typically, these methods involve grinding the neem seeds in a mill to about 5 mesh. The ground neem seeds are then extracted with hexane to remove the neem oils. For example, two kgs. of ground neem seeds are added to 10 liters of hexane and agitated mildly for 24 hours. After the hexane extraction the seeds are separated from the hexane by filtration or centrifugation. The neem oil is then recovered from the hexane. The neem oil is used in amounts of about 0.01 to about 0.75 weight % and preferably about 0.1 to about 0.5 weight % of the total gum composition.

The preparation of neem oil, the application thereof including as a component of toothpastes, mouthwashes, food compositions and the like and uses thereof such as in the treatment of gingivitis, for reducing caries and treatment of inflammation of the mouth, as a natural flavoring agent in oral compositions for treating plaque and gingivitis are known and have been described in Walter H. Lewis, *Medical Botany-Plants Affecting Man's Health*, 246–47 (John Wiley & Sons 1977) (herein-after *"Medical Botany"*); Maurice M. Iwu, *Handbook of African Medicinal Plants*, 124–28 (CRC Press 1993); U.S Pat. Nos. 5,371,254; 5,472,684 and HI 541, the foregoing for their teachings relating to neem oil, are incorporated herein by reference in their entirety.

The use of sodium bicarbonate in dentifrices, particularly for effective cleansing and deodorizing is known. Sodium bicarbonate is used in the compositions of the invention in an amount of about 0.50 to about 1.0 weight % of the total gum composition. An advantage to the use of sodium bicarbonate and peroxide is that they combine in the presence of the water in the mouth to release little oxygen bubbles. These oxygen bubbles get to the tiny spaces between the teeth and around the gum line enhancing the overall whitening effect.

The parsley extract is present in an amount of about 0.05 to about 0.50 weight % and preferably 0.1 to 0.4 weight % is present for its properties as a flavorant and breath freshener.

The sodium percarbonate, sodium bicarbonate, parsley extract and neem oil taken together comprise the active ingredients of the gum composition and are present in an amount of from about 0.50 to about 3.00 wt. % of the total composition and preferably about 2.00 wt. % of the total composition.

The non-active ingredients include for example the following: gum base, hydrogenated starch hydrolysate, soy lecithin, sorbitol or maltitol, glycerin, flavorants, calcium carbonate, titanium dioxide, vitamin C (as calcium ascorbate), vitamin E (as di-α-tocopheryl acetate), sodium copper chlorophyll and possibly other optional ingredients as have been disclosed earlier in this description present in the total comprise about 97–99 wt. % of the total composition.

Again, as used herein the term "chewing gum" is intended to mean a composition which comprises a substantially water-insoluble, chewable plastic gum base such as chicle, or substitutes therefor, including jelutung, guttakay rubber and/or certain comestible natural or synthetic resins or waxes. Incorporated within the gum base, in admixture therewith may be plasticizers or softening agents, e.g. glycerine; and a flavoring composition and, in addition, sweetening agents which may be sugars, including sucrose or dextrose and/or artificial sweeteners including dipeptides, cyclamates, aspartane and saccharin. Other optional ingredients may also be present.

The following essential oils are preferably used as flavoring oils: peppermint oil, spearmint oil, mixtures of peppermint oil and spearmint oil, clove oil, bay oil, anise oil, eucalyptus oil, thyme oil, cedar leaf oil, parsley seed oil, sweet oil of birch, cinnamon oil, oil of nutmeg, oil of sage, oil of bitter almonds, cassia oil, and methylsalicylate (oil of wintergreen). Xylitol may also be included as it is known as an anticaries preparation.

The active ingredients comprise about 0.5 to about 3.0 wt. % of the total ingredients, while the gum base and non-active ingredients comprise about 97 to about 99.0% of the total composition.

The non-active ingredients include both solids and liquids which are ingestible, non-toxic materials. Substances suitable for use herein as ingredients to be combined with the gum base for example, flavoring adjuvants are well known in the art for such use being extensively described in the relevant art. In addition to the requirements that the material selected be ingestible and thus non-toxic or otherwise non-deleterious are the additional requirements that the selected material be compatible with the active ingredients, particularly with the sodium carbonate peroxyhydrate and that such material be non-reactive within the range of storage conditions and room temperature use conditions with the sodium carbonate peroxyhydrate.

In general, the gum base is prepared by heating and blending various ingredients, such as, natural gums, synthetic resins, waxes, plasticizers, etc., in a manner well known in the art. Typical examples of a chewing gum base are masticatory substances of vegetable origin, such as chicle, crown gum, nispero, rosidinha, jelutong, pendare, perillo, niger gutta, tunu, etc., masticatory substances of synthetic origin, such as butadiene-styrene polymer, isobutylene-isoprene copolymer, petroleum wax, polyethylene, polyisobutylene, etc. (see above).

Conventionally, chewing gum base and chewing gum products are manufactured using separate mixers, different mixing technologies and, often, at different factories. One reason for this is that the optimum conditions for manufacturing gum base, and for manufacturing chewing gum from gum base and other ingredients such as sweeteners and flavors, are so different that it is impractical to integrate both tasks. Chewing gum base manufacture, on the one hand, involves the dispersive (often high shear) mixing of difficult-to-blend ingredients such as elastomer, filler, elastomer plasticizer, base softeners/emulsifiers and, sometimes wax, and typically requires long mixing times. Chewing gum product manufacture, on the other hand, involves combining the gum base with more delicate ingredients such as product softeners, bulk sweeteners, high intensity sweeteners and flavoring agents using distributive (generally lower shear) mixing, for shorter periods.

In the present instance, in order to improve the efficiency of providing the gum base needed in gum product manufacture, the gum base is separately manufactured or purchased from a reliable source for example, Dreyfus of South Plainfield, N.J.

The chewing gum products can be made in the conventional manner. The gum base is mixed with the other ingredients in a ribbon blender with jacketed sidewalls of the type manufactured by Baker Perkins Co. The resultant material is formed directly into slabs of the desired size or into larger slabs which are then cut to desired size, i.e., ⅙"×3"×0.1." Alternatively the gum mixture can be made into tablets again using readily available equipment and procedures.

Preferably, the following procedure is followed: Flavored chewing gum compositions are prepared according to the base formulation below:

| GUM INGREDIENTS | WT % |
|---|---|
| Dreyco ® gum base (Dreyfus) | 15.00–70.00 |
| Sorbitol and/or maltitol | 27.00–82.00 |
| Flavoring for example natural mint flavor (Silesia) | 0.50–0.80 |
| Alkali metal percarbonate | 0.30–0.75 |
| Neem oil | 0.20–0.75 |
| Sodium bicarbonate | 0.20–1.00 |
| Parsley extract | 0.30–0.50 |

The gum base is introduced into a mixing kettle equipped with two Z-arms and a jacket maintained at a temperature of 50° C. by circulation of water within the jacket. After blending the gum base for about 5 minutes, about ⅓ of the sorbitol and/or maltitol is added and mixed intimately with the gum base. The mixture is blended continuously for 2–5 minutes, followed by addition of a second ⅓ of the sorbitol and/or maltitol. After blending for 2–5 minutes the remaining amount of the sorbitol and/or maltitol and the flavoring agent are introduced. Finally after blending for 2–5 minutes, the alkali metal percarbonate, the sodium bicarbonate, parsley extract and neem oil are introduced. Blending is continued for a further 2 minutes so as to obtain a homogeneous paste. If stick gum is to be produced, the paste is then removed from the kneading machine, laminated and cut into sticks millimeters in thickness. Tablets can also be formed from the paste and coated with a suitable tablet gum coating.

The following examples represent preferred embodiments and further illustrate the present invention without however limiting the same thereto.

EXAMPLE I:

A teeth whitening gum is prepared from the following ingredients:

| | WT % |
|---|---|
| GUM INGREDIENTS | |
| Gum base (Dreyco ® Dreyfus) | 28.00 |
| Hydrogenated starch hydrolysate | 11.95 |
| Sorbitol powder | 55.25 |
| Soy lecithin | 0.80 |
| Vegetable glycerin | 1.00 |

-continued

| | WT % |
|---|---|
| Flavor oils | 1.00 |
| Subtotal | 98.00 |
| ACTIVE INGREDIENTS | |
| Sodium Carbonate Peroxyhydrate | 0.35 |
| Sodium bicarbonate | 0.95 |
| Parsley extract | 0.35 |
| Neem Oil | 0.35 |
| Subtotal | 2.00 |
| Total | 100.00 |

In this example, the gum base is introduced into a kettle, melted in the temperature range of 175°–250° F. and placed in a standard dough mixer kettle equipped with sigma blades.

The remaining gum ingredients are added to the preheated gum base. After 3–7 minutes of mixing, the active ingredients are added and blended with the above mixture for 5 minutes at 120°–150° F. The resulting gum is discharged from the kettle and formed into sticks or tablets employing the conventional techniques and equipment and then wrapped.

The chewing gum product obtained in either case is found to be stable and in use to function in whitening the user's teeth and to also improve cleaning and the condition of the gums.

EXAMPLE II

| | WT % |
|---|---|
| GUM INGREDIENTS | |
| Gum base (Dreyco ® Dreyfus) | 30.00 |
| Hydrogenated starch hydrolysate | 12.00 |
| Sorbitol | 48.00 |
| Lecithin | 1.00 |
| Glycerin | 0.70 |
| Flavor oils | 1.00 |
| Subtotal | 92.70 |
| ACTIVE INGREDIENTS | |
| Sodium carbonate peroxyhydrate | 0.40 |
| Sodium bicarbonate | 0.90 |
| Parsley extract | 0.35 |
| Neem oil | 0.35 |
| Subtotal | 2.00 |
| Total | 94.70 |

The balance of 5.3 wt % consisted of xylitol, vitamin C, vitamin E, sodium copper chlorophyll and spearmint oil, with xylitol comprising the major component.

The method of preparation disclosed with respect to Example I was followed and the composition formed into tablets which were coated with a conventional spearmint flavored coating. Each coated tablet weighed about 2.0 grams.

I claim:

1. A teeth whitening chewing gum, comprising 1) a water-insoluble gum base, a flavorant, a sweetener and a plasticizer as the inactive ingredients; and 2) alkali metal carbonate peroxyhydrate, sodium bicarbonate, parsley extract and neem oil as active ingredients wherein said gum inactive ingredients comprise from about 97 to about 99 wt. % of the total gum composition.

2. A teeth whitening chewing gum according to claim 1 wherein said carbonate peroxyhydrate is sodium carbonate peroxyhydrate.

3. A teeth whitening chewing gum according to claim 1 wherein said gum ingredients comprise about 98 wt. % of said total gum composition.

4. A teeth whitening chewing gum according to claim 1 wherein said active ingredients comprise from about 0.5 to about 3.0 wt. % of the total composition.

5. A teeth whitening chewing gum according to claim 1 wherein said active ingredients are present in an amount of about 2.0 wt. % of said total gum composition.

6. A teeth whitening chewing gum according to claim 1 wherein said gum ingredients comprise about 98 wt. % and said active ingredients about 2 wt. % of said total gum composition.

7. A teeth whitening chewing gum according to claim 1 wherein said gum base is a member selected from the group consisting of a member selected from the group consisting of polyisobutylene, isobutyleneisoprene copolymers, styrene-butadiene copolymers, polyvinyl acetate, polyisoprene, polyethylene, vinyl acetate - vinyl laurate copolymers, natural rubber and combinations thereof.

8. A teeth whitening chewing gum according to claim 1 wherein said flavorant is a member selected from the group consisting of peppermint oil, spearmint oil, mixtures of peppermint oil and spearmint oil, clove oil, bay oil, anise oil, eucalyptus oil, thyme oil, cedar leaf oil, cinnamon oil, oil of nutmeg, oil of sage, oil of bitter almonds, cassia oil, and methylsalicylate.

9. A teeth whitening chewing gum according to claim 1 wherein said sweetener is a member selected from the group consisting of sucrose, dextrose, dipeptides, cyclamates and saccharin.

10. A teeth whitening chewing gum according to claim 1 wherein said plasticizer is a member selected from the group consisting of lanolin, stearic acid, sodium stearate and potassium stearate.

11. A teeth whitening chewing gum according to claim 1 comprising:

|  | WT % |
|---|---|
| GUM INGREDIENTS | |
| Gum base | 28.00 |
| Hydrogenated starch hydrolysate | 11.95 |
| Sorbitol powder | 55.25 |
| Soy lecithin | 0.80 |
| Vegetable glycerin | 1.00 |
| Flavor oils | 1.00 |
| Subtotal | 98.00 |
| ACTIVE INGREDIENTS | |
| Sodium Carbonate Peroxyhydrate | 0.35 |
| Sodium bicarbonate | 0.95 |
| Parsley extract | 0.35 |
| Neem oil | 0.35 |
| Subtotal | 2.00 |
| Total | 100.00 |

12. A teeth whitening chewing gum according to claim 11 in stick form.

13. A teeth whitening gum chewing according to claim 11 in tablet form.

14. A process for whitening teeth which comprises chewing the chewing gum according to claim 1.

* * * * *